(12) United States Patent
Massholder

(10) Patent No.: US 6,258,736 B1
(45) Date of Patent: Jul. 10, 2001

(54) DEVICE WITH AT LEAST ONE SURFACE LAYER

(76) Inventor: Karl Massholder, Panoramaweg 27, D-69250 Schoenau (DE)

( * ) Notice: Subject to any disclaimer, the term of this patent is extended or adjusted under 35 U.S.C. 154(b) by 0 days.

(21) Appl. No.: 09/331,651

(22) PCT Filed: Dec. 23, 1997

(86) PCT No.: PCT/EP97/07252

§ 371 Date: Aug. 23, 1999

§ 102(e) Date: Aug. 23, 1999

(87) PCT Pub. No.: WO98/28012

PCT Pub. Date: Jul. 2, 1998

(30) Foreign Application Priority Data

Dec. 23, 1996 (DE) .............................. 196 54 109

(51) Int. Cl.[7] .............................................. H01L 21/477
(52) U.S. Cl. .......................... 438/795; 422/22; 422/24; 426/236; 426/237
(58) Field of Search .................... 422/186.3, 24, 422/22; 438/795; 250/423; 204/24; 426/236, 237; 134/1

(56) References Cited

U.S. PATENT DOCUMENTS

| | | | |
|---|---|---|---|
| 5,045,509 | * | 9/1991 | Kiefer ................................ 501/59 |
| 5,151,135 | * | 9/1992 | Magee et al. ...................... 134/1 |
| 5,439,595 | * | 8/1995 | Downey, Jr. ...................... 210/748 |
| 5,449,443 | * | 9/1995 | Jacoby et al. ..................... 204/157.3 |
| 5,677,113 | * | 10/1997 | Suzuki et al. ..................... 430/329 |
| 5,778,664 | * | 7/1998 | Janata et al. ..................... 60/274 |
| 5,817,181 | * | 10/1998 | Okamura et al. .................. 134/1.1 |
| 5,821,175 | * | 10/1998 | Engelsberg ........................ 438/795 |
| 5,865,959 | * | 2/1999 | Meinzer et al. ................... 204/157.3 |
| 5,875,384 | * | 2/1999 | Peill et al. ....................... 422/186.3 |
| 5,902,751 | * | 5/1999 | Godec et al. ..................... 436/146 |
| 5,919,422 | * | 7/1999 | Yamanaka et al. ................ 422/121 |
| 6,004,667 | * | 12/1999 | Sakurada et al. ................. 428/323 |
| 6,024,929 | * | 2/2000 | Ichikawa et al. ................. 422/186 |

FOREIGN PATENT DOCUMENTS

| | | | |
|---|---|---|---|
| 0 714 041 | | 5/1919 | (EP) . |
| 590 477 A1 | | 9/1993 | (EP) . |
| 09118604 | * | 5/1997 | (JP) .............................. A61F/13/02 |
| 08288898 | * | 5/1998 | (JP) .............................. B03C/3/60 |
| 10190058 | * | 7/1998 | (JP) .............................. H01L/33/00 |

OTHER PUBLICATIONS

Database WPI, Section PQ, Week 9648 Derwent Publications, Ltd., London, GB; Class P41 AN 96–480395 XP002069934 & JP 08 243 434 A (Ebara Corp)—1996.

* cited by examiner

Primary Examiner—Matthew Smith
Assistant Examiner—Renzo N. Rocchegiani
(74) Attorney, Agent, or Firm—Foley & Lardner

(57) ABSTRACT

The proposal is for a device with at least one surface layer (1) made from a semiconductor material (4) having an inner side (15), which rests on a support (3), and a disinfectable and/or oxidizing outer side (2), and with a UV radiation source (6), in which device the support (3) conducts light, UV radiation (13) from the UV radiation source (6) is input directly on to the inner side (15) of the semiconductor material (4) via the light-conducting support (3). The light-conducting support (3) and the surface layer (1) of the semiconductor material (4) lying thereon can be applied to the surface of a piece of equipment which is to be disinfected or may even form this piece of equipment.

20 Claims, 1 Drawing Sheet

DEVICE WITH AT LEAST ONE SURFACE LAYER

Figure 1:
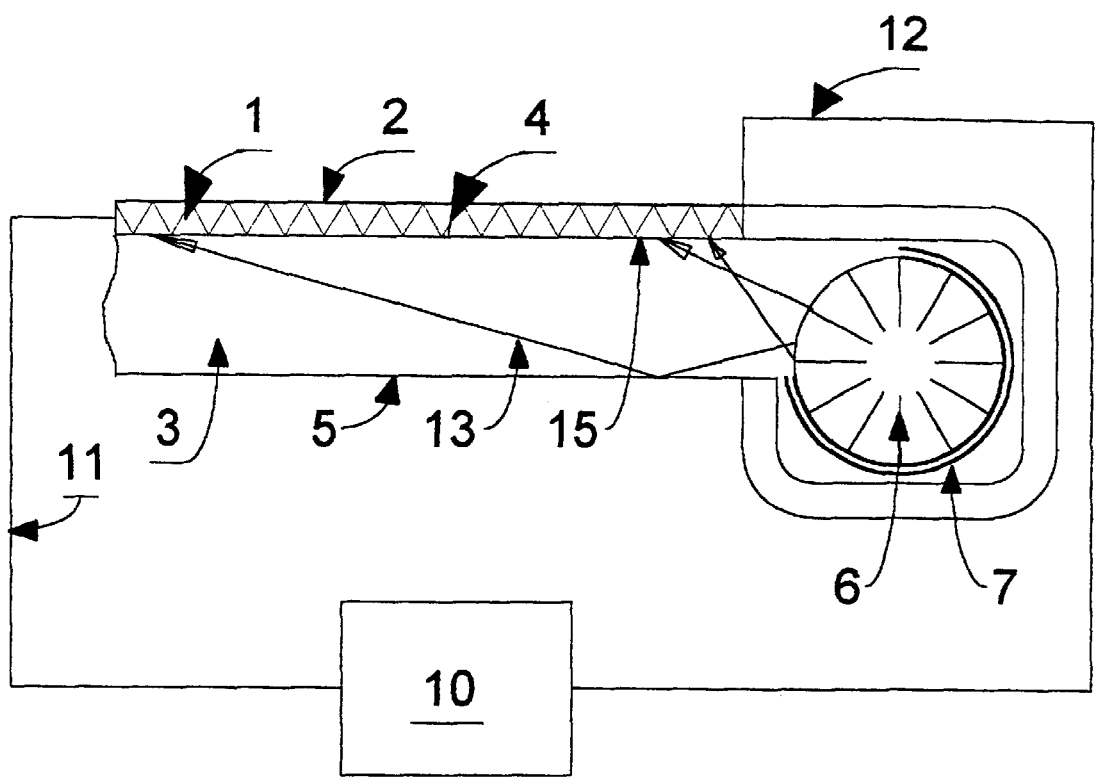

The invention relates to a device having at least one surface layer with a disinfectable and/or oxidizing outer side. The invention furthermore relates to a method for disinfection and/or oxidation on the outer side of a surface layer.

Hygiene plays an important role in many areas of modern life. These include in particular the field of health. For example, in hospitals or doctor's surgeries, certain areas or pieces of equipment, such as operating tables, have to be kept as free from germs as possible, or even completely germ-free. It is also necessary to pay considerable attention to hygiene when handling foodstuffs which are intended for human consumption. This applies, for example, to sale counters for foodstuffs, work surfaces in companies which process foodstuffs, such as butcher's shops or restaurants, but also dairies, including their beverage lines. Research, diagnostics and administration in the fields of microbiology and biotechnology should also be mentioned, in addition to a considerable number of further applications.

In all these fields, it is desirable or even necessary for certain surfaces to be kept free from germs as far as possible or even completely. The same applies to internal surfaces of containers, pipelines and valves.

To do this, it is known for open surfaces to be kept clean by mechanical cleaning with bactericidal agents. If appropriate, equipment can be sterilized using elevated temperatures. In certain cases, irradiation with UV light is also employed. However, this is not always fully effective and, in addition, often causes considerable problems with regard to the danger or strain imposed on people, and therefore large-scale UV disinfection operations are only carried out at times when no work is being done, e.g. overnight.

The drawback of the known cleaning methods is that germs begin to build up again immediately after the cleaning operation has taken place. The bactericidal action is dependent on the care taken by the cleaning staff and on the cleaning intervals. A highly sterilized state can therefore only be maintained with great difficulty and a high level of outlay. A further difficulty is that some bacteria build up a certain resistance to the bactericidal agents, so that in fact sterilization is impossible, or not sufficiently possible, even despite strenuous efforts. Under certain circumstances, this problem will often not be noticed.

An even more difficult problem is the cleaning of internal surfaces which can only be rinsed or sterilized with the aid of steam. Rinsing constantly produces dead spaces and "cold" areas which are not affected by the cleaning work. This may result in the formation of colonies of bacteria, promoting subsequent germ formation. Moreover, operations have to be suspended for cleaning. The same also applies to external surfaces. For toxicological reasons, large-scale disinfecting measures using formaldehyde or ethylene oxide present considerable problems, since these gases penetrate into the material and are released over relatively long periods (e.g. quarantine stations). As a result, it is necessary to keep a larger stock of instruments or rooms ready, since availability is limited as a result of these times when gases are being released.

The invention is based on the object of providing a device having at least one surface layer, with an outer side which can be disinfected relatively easily and with a relatively high reliability and/or has an oxidizing action.

A further object of the invention is to provide a device which makes it possible to disinfect internal surfaces which cannot be reached by direct irradiation with UV light. Another object of the invention is to provide a method for disinfection and/or cleaning on the outer side of a surface layer.

The invention is based on a device with at least one surface layer made from a semiconductor material having an inner side, which rests on a support, and a disinfectable and/or oxidizing outer side, and with a UV radiation source.

The device is then characterized in that the support conducts light, and in that UV radiation from the UV radiation source is input directly on to the inner side of the semiconductor material via the light-conducting support.

Light guides are arrangements of optical components for guiding light onwards by means of total reflection, the reduction in the refractive index inside the light guide from the inside outwards playing a particularly significant role. For a good light guide, it is desirable for the light losses brought about by absorption, scattering and radiation to be kept as low as possible. It has now surprisingly been found that the low, hitherto undesirable outwards emission of radiation along an optical waveguide is sufficient to activate the inner side of a semiconductor which has been applied thereto and thus to bring about disinfection and/or oxidation.

It is therefore possible for the objects or work surfaces which it is desired to clean or disinfect to be provided with the light-conducting support and the surface layer made from a semiconductor material. However, it is also possible for the objects which are to be disinfected or cleaned themselves to be designed as light-conducting supports and for the surface layer made from the semiconductor material to be applied thereto.

In order to simplify the following explanation, the following text always refers to "disinfection", even if only a reduction in the number of germs on the surface takes place. Although in many cases complete sterilization is possible, it is not always necessary or desired.

To disinfect the surface layer, the UV light source is started up so that it emits UV radiation. However, this UV radiation is directed towards the inner side or rear side, which is not visible from the outside, of the semiconductor material. It is therefore entirely possible for the surface to be covered with tools or other equipment which could lead to shadows in the event of the outer side being irradiated. The UV radiation no longer has to emerge on the outside in order to bring about the desired disinfection. Although the biological, physical and chemical processes involved have not yet been fully explained, it is assumed that the UV radiation excites the semiconductor material, i.e. photoactivates the material. Photoactivation means that the light absorption in the semiconductor, e.g. $n-TiO_2$, causes electrons to be lifted from the valence band into the conduction band. The result is a redox potential which kills germs via the formation of radical species or mechanisms. Since these processes are unspecific, oxidative degradation reactions also occur in addition. Since the semiconductor is not changed, it is called a catalyst. Thus the surface which is irradiated from the inside is disinfected in a simple manner. Disinfection of this nature may even take place during normal use, so that complete or at least substantial sterilization can be maintained even during operation.

A light-conducting support is arranged between the UV light source and the inner side. This makes it possible to select the arrangement of the UV light source in relation to the surface layer more freely. In certain cases, it is not possible to arrange the light source on the rear side or inner side of the surface layer, since there is no space available there. If a light-conducting support is now used, the UV radiation can also be guided on to the inner side of the semiconductor material from other locations.

The light-conducting support may preferably be configured as a panel, for example as the table top of an operating table. In this case, the panel-like support is preferably coated on one side, but if necessary on both sides, with semiconductor material.

However, it is also possible to design the light-conducting support in the form of a tube, so that pipelines can be made available as cut-to-length stock, including the connection fittings. In the case of supports which are designed in the form of a tube, it is preferable for the inner surface of the tube to be coated with the semiconductor material, although it is also possible for tube-like supports to be coated with the semiconductor material on the outer surface of the tube.

Furthermore, the light-conducting support may be designed as a container, the inner surface of which is coated with the semiconductor material. However, it is also possible to provide the inner surface of a container made from any desired material with the light-conducting support and then with the semiconductor material. Containers with disinfectable inner surfaces are, for example, storage tanks.

The light-conducting support may be rigid, but it is also possible to use deformable, elastic, flexible materials as light-conducting supports. Flexible, hose-like supports with the semiconductor material preferably applied to the outer surface provide catheters used in medicine. Furthermore, fibres, woven fabrics or non-woven fabrics may be used as flexible, light-conducting support materials.

The support material may preferably be quartz or a light-conducting polymer material. Suitable light-conducting polymer materials are, for example, fluoropolymers or polymethylmethacrylate.

Light-conducting polymer materials may be of very flexible design and, at the same time, are relatively insensitive to mechanical loads. It is therefore also possible to provide surfaces which are not planar with a surface layer. In addition, there are a number of polymers which transmit UV light.

The semiconductor material is preferably applied in a thin layer to the light-conducting support material. When irradiated with UV light, the light-conducting support material allows the radiation to pass through and impinge on the semiconductor material from the inner side. Thus the support material has the role not only of holding the semiconductor but also of conducting the light. The surface layer can therefore be made relatively thin.

Preferably, the support material reflects towards the semiconductor material at least on the side lying opposite to the semiconductor material. A configuration of this nature may advantageously be utilized to introduce the UV radiation into the support material from the side. Since radiation of this nature always has a specific radiation angle, i.e., roughly speaking, the radiation forms a radiation cone, part of the UV radiation will be incident directly on the inner side of the semiconductor material, while another part of the radiation will be incident on the "bottom" of the support material. However, from there the radiation is reflected back towards the semiconductor material, so that even relatively great widths or lengths can be supplied from a UV light source arranged at the side or at the end.

Preferably, the semiconductor material is formed as a thin layer on the support material. Therefore, it is preferable for the semiconductor material to cover the entire surface of the support material. There is thus no risk of the UV radiation being transmitted outwards. Disinfection can therefore be carried out irrespective of whether or not there are people in the vicinity.

In this case, it is particularly preferred for the semiconductor material to have a thickness in the order of magnitude of a few molecules. In this case, the excitation of the "bottom" molecules of the layer of semiconductor material, i.e. those molecules on which the UV light acts directly, very quickly leads to a corresponding activation of the top molecules in the semiconductor layer, which then leads to inactivation of the germs or bacteria.

In addition, or as an alternative, the semiconductor material may also be contained in a liquid which is present on the surface layer. For example, it is possible to add the semiconductor material as a "cleaning agent". Disinfection of the surface is also achieved if the liquid is then applied, for example by wiping or spraying, and then, or at the same time the UV light source is actuated.

The semiconductor material is preferably formed by titanium dioxide or silicon carbide. These materials are available at low cost. They have proven useful in the disinfection of surfaces which are provided with a surface layer of this nature.

Preferably, the wavelength of the UV radiation lies in the range from 280 to 400 nm, in particular in the range from 320 to 380 nm.

Normally, the disinfecting action of UV radiation occurs only at a wavelength of approx. 254 nm. However, this wavelength is hazardous for humans owing to its mutagenic effect on skin cells and its particularly harmful effect on the eyes. However, the claimed wavelength in the range from 280 to 400 nm, in particular 320 to 380 nm (UVA), is not dangerous. UV light in this wavelength is even used for cosmetic and therapeutic purposes. Particularly if a wavelength range of 350 nm or higher is selected, the use of a wavelength of this nature has the advantage that the UV light cannot be seen, and in particular is not blinding.

In a preferred configuration, there is provision for a fluorescent dye to be arranged in the semiconductor material and/or in the UV light source and/or in the light-conducting support. This fluorescent dye may, for example, be embedded in a polymer. This polymer may be the transparent support material or another light guide.

Incorporating the fluorescent dye makes it possible to monitor visually whether or not the UV light source is operating. Furthermore, this configuration has the advantage that UV light of this wavelength can be conducted by mouldable polymers. The UV radiation of approx. 254 nm which has hitherto been used for disinfection could only be conducted via quartz conductors.

In addition, the fluorescent dye acts, as it were, as a light transformer. It converts UV radiation which is emitted from the UV light source in a relatively broad spectrum into radiation with a relatively narrow wavelength range defined by the dye in question. In this way, the energy of the UV light source can be utilized even better.

In addition to the UV light source, it is also possible to use an excitation device which electrically excites the semiconductor material. Electrical excitation is also able to produce free valences, i.e. lift electrons from the valence band into the conduction band, an effect which again inactivates the germs by means of the redox potential discussed above.

The invention is described below with reference to a preferred exemplary embodiment in conjunction with the drawing, in which:

The single FIGURE shows a diagrammatic cross section through a device according to the invention.

The inner side 15 of the surface layer 1 made from a semiconductor material 4 rests on a light-conducting support. The outer side of the surface layer then forms the disinfectable and/or oxidizing surface. The surface layer with the disinfectable and/or oxidizing outer side and the light-conducting support on which the inner side of the surface layer rests can be applied to a piece of equipment (not shown in more detail), for example a work top or operating table, to the inner wall of a container or to the inner wall or outer wall of a tube. However, it is also possible for a piece of equipment itself, for example an operating table, pipelines or catheters, to be designed as light-conducting supports on which a semiconductor material rests. The light-conducting, UV-transparent support material may, for example, be formed by a light-conducting polymer material. Polymers of this nature have the advantage that they can also be applied to surfaces retroactively.

Titanium dioxide ($TiO_2$) or silicon carbide, for example, are suitable for the semiconductor material 4, which is applied in particular as a thin layer, preferably with a layer thickness in the order of magnitude of a few molecules.

On that side 5 which is opposite to the outer side 2 and, for the sake of simplicity, is also referred to as the underside, the support material 3 is designed to be reflective, i.e. the underside 5 reflects light which is incident from the direction of the outer side 2 back towards the outer side 2.

These reflective properties are important in particular in connection with UV radiation. For this purpose, the device has a UV light source 6 which emits UV radiation at a wavelength in the range from 280 to 400 nm, in particular in the range from 320 to 380 nm. The UV light source is provided with a reflector 7 which directs the UV radiation emitted from the UV light source 6 laterally into the transparent and light-conducting support material 3. As can be seen from the arrows 13, part of the radiation is incident directly on the inner side of the layer 4 of semiconductor material. A further part of the UV radiation is reflected from the underside 5 of the support material 3 towards the layer of semiconductor material.

If there were to be no room at the position illustrated for the UV light source 6, the UV radiation may also be guided via suitable optical fibres until it reaches the appropriate location for introduction into the support material.

In addition, a fluorescent dye may, in a manner which is not shown, be arranged between the layer 4 of semiconductor material and the UV light source 6, for example in the support material 3 or in another light guide. This fluorescent dye serves as a "light transformer", i.e. it is excited by the UV radiation of the light source 6 even if this radiation contains a relatively broad spectral range of the UV light. It then, however, emits UV light with a relatively narrow spectral range or even with only a single wavelength. If this wavelength or the narrow spectral range is suitably adapted to the semiconductor material, it is possible to achieve an excellent level of utilization of the energy from the light source 6.

Although only a thin layer 4 of the semiconductor material is applied to the support material 3, this layer is sufficient to prevent the UV radiation from being transmitted outwards, or at least to reduce this transmission to a sufficient extent for an observer not to experience any unpleasant sensation or to be inconvenienced or put in danger in any way. The layer 4 is only a few molecules thick. When UV radiation from the light source 6 then impinges on the inner side of the layer 4, the semiconductor, for example $TiO_2$, is then excited in that area. It is assumed that an electron migrates "inwards", i.e. is lifted to a different energy level. The result is a free valence which, if a germ is present at this location, oxidizes and therefore inactivates this germ. Since the semiconductor layer 4 covers the entire surface of the support material and the UV radiation from the UV light source 6 acts on the entire layer 4 from the inside, every germ on the surface is correspondingly oxidized and therefore inactivated.

In addition to the excitation of the semiconductor material in the layer 4 by means of UV radiation which is incident from the rear side, it is also possible to use electrical excitation. For this purpose, an electrical excitation device 10 is provided and is connected to the layer 4 via two electrodes 11, 12. An electrical excitation can be used to assist the excitation of the semiconductor material by means of the UV radiation.

The use of the surface layer 1 resting on a support 3 is not limited to planar surfaces. Thus it is not only work surfaces, tables, walls, bases or outer sides of any equipment which can be provided with or formed from this structure. It is also possible, for example, to apply a surface layer of this nature to the inner wall of pipes or of objects shaped in any way. This may even be carried out retroactively by, for example, introducing light-conducting polymers into existing pipelines, as is already being done for the purpose of stemming corrosion. The layer 4 may be permanently applied to the support material 3. As an alternative, the layer 4 may also be applied only for cleaning purposes, for example with the aid of a liquid which contains the semiconductor material in finely-ground form.

What is claimed is:

1. A device comprising:
   at least one surface layer having an inner side which rests on a light-conducting support and with an outer side, and
   a UV radiation source, wherein the surface layer is formed from a semiconductor material, wherein UV radiation from the UV radiation source is input directly onto the inner side of the semiconductor material via the light-conducting support, the outer side of the surface layer being one or more of disinfected or having an oxidizing effect, and wherein the support is designed as a container whose inner surface is coated with the semiconductor material.

2. A device comprising:
   at least one surface layer having an inner side which rests on a light-conducting support and with an outer side, and
   a UV radiation source, wherein the surface layer is formed from a semiconductor material, wherein UV radiation from the UV radiation source is input directly onto the inner side of the semiconductor material via the light-conducting support, the outer side of the surface layer being one or more of disinfected or having an oxidizing effect, and, wherein a fluorescent dye is arranged in one or more of the semiconductor material, the UV light source or the light-conducting support.

3. A device comprising:
   at least one surface layer having an inner side which rests on a light-conducting support and with an outer side, and
   a UV radiation source, wherein the surface layer is formed from a semiconductor material, wherein UV radiation from the UV radiation source is input directly onto the inner side of the semiconductor material via the light-conducting support, the outer side of the surface layer being one or more of disinfected or having an oxidizing effect, and wherein an excitation device which electrically excites the semiconductor material is provided in addition to the UV light source.

4. A disinfecting device comprising:
   at least one surface layer in contact with a foodstuff or germs having an inner side that rests on a light-conducting support, and
   a UV radiation source, wherein the surface layer is formed from a semiconductor material, and wherein UV radiation from the UV radiation source is inputted directly onto the inner side of the semiconductor material via the light-conducting support, the outers side of the surface layer being disinfected.

5. A disinfecting device according to claim 4, wherein the at least one surface layer and the light conducting support are applied on a surface to a piece of equipment.

6. A disinfecting device according to claim 5, wherein the piece of equipment is selected from the group consisting of a work top for handling foodstuffs, an operating table, a container, a pipeline, and a catheter.

7. A disinfecting device according to claim 4, wherein the light conducting support is formed into a piece of equipment.

8. A disinfecting device according to claim 7, wherein the piece of equipment is selected from the group consisting of a work top for handling foodstuffs, an operating table, a container, a pipeline, and a catheter.

9. A disinfecting device according to claim 4, wherein a fluorescent dye is arranged in one or more of the semiconductor material, the UV light source, or the light conducting support.

10. A disinfecting device according to claim 4, wherein the support material comprises quartz or a light conducting polymeric material.

11. A disinfecting device according to claim 4, wherein the support is plastically or elastically deformable.

12. A disinfecting device according to claim 4, wherein the semiconductor material is formed as a thin layer.

13. A disinfecting device according to claim 4, wherein the semiconductor material is titanium dioxide or silicon carbide.

14. A disinfecting device according to claim 4, wherein the support comprises polymethylmethacrylate.

15. A method for disinfecting a surface in need of disinfecting comprising:
    providing a light conducting support having the surface layer in need of disinfecting, wherein the surface layer comprises a semiconductor material and the inner side of the surface layer rests on the support;
    providing a UV radiation source;
    directing UV radiation from the UV radiation source onto the support, through the support and onto the inner side of the semiconductor material by light conduction; and
    continuing to direct the UV radiation for a time sufficient to disinfect the surface layer.

16. A method for disinfecting according to claim 15, wherein the surface layer in need of disinfecting and the light conducting support are applied on a surface to a piece of equipment.

17. A method for disinfecting according to claim 16, wherein the piece of equipment is selected from the group consisting of a work top for handling foodstuffs, an operating table, a container, a pipeline, and a catheter.

18. A method for disinfecting according to claim 15, wherein the light conducting support is formed into a piece of equipment.

19. A method for disinfecting according to claim 18, wherein the piece of equipment is selected from the group consisting of a work top for handling foodstuffs, an operating table, a container, a pipeline, and a catheter.

20. A method for disinfecting according to claim 15, wherein a fluorescent dye is arranged in one or more of the semiconductor material, the UV light source, or the light conducting support.

* * * * *